United States Patent [19]

Weinstock et al.

[11] 4,229,652
[45] * Oct. 21, 1980

[54] BACKSCATTER APPARATUS AND METHOD FOR MEASURING THICKNESS OF A CONTINUOUSLY MOVING COATED STRIP OF SUBSTRATE MATERIAL

[75] Inventors: Jacques Weinstock, Flushing; Derek Lieber, North Merrick; William D. Hay, Peekskill, all of N.Y.

[73] Assignee: Unit Process Assemblies, Inc., Syosset, N.Y.

[*] Notice: The portion of the term of this patent subsequent to Sep. 19, 1995, has been disclaimed.

[21] Appl. No.: 911,974

[22] Filed: Jun. 2, 1978

Related U.S. Application Data

[63] Continuation of Ser. No. 803,250, Jun. 3, 1977, Pat. No. 4,115,690.

[51] Int. Cl.³ .............................................. G01N 23/00
[52] U.S. Cl. .................................... 250/308; 250/360
[58] Field of Search .................. 250/308, 358 R, 359, 250/360, 272, 273, 277

[56] References Cited

U.S. PATENT DOCUMENTS

| 3,621,259 | 11/1971 | Boissevain | 250/360 |
| 4,115,690 | 9/1978 | Weinstock et al. | 250/308 |

Primary Examiner—Alfred E. Smith
Assistant Examiner—Janice A. Howell
Attorney, Agent, or Firm—Nims, Howes, Collison & Isner

[57] ABSTRACT

A backscatter measurement device for measuring the thickness of a coating on a strip of substrate material moving from a feed supply to a take up location at a predetermined speed. A measurement wheel is provided on the rim of which are mouted backscatter probes for irradiating and detecting the backscattered radiation from the coated substrate. The coated strip of substrate material is threaded around the outer surface of the rim. The measurement wheel is rotated at a speed such that the tangential speed of a point on the rim equals the speed of the moving strip whereby the probe and an adjacent point on the strip are stationary relative to one another while the point on the strip is adjacent the rim. Thus thickness measurements may be taken without stopping the movement of the coated strip.

7 Claims, 3 Drawing Figures

BACKSCATTER APPARATUS AND METHOD FOR MEASURING THICKNESS OF A CONTINUOUSLY MOVING COATED STRIP OF SUBSTRATE MATERIAL

This is a continuation of application Ser. No. 803,250, filed June 3, 1977, now U.S. Pat. No. 4,115,690.

BACKGROUND OF INVENTION

This invention relates to backscatter thickness measuring instruments and particularly to a device for measuring the thickness of a coating on a strip of substrate material moving from a feed supply to a take-up location at a predetermined speed.

Backscatter instruments are used to measure thickness of coatings by irradiating a coating on a substrate and counting the particles backscattered therefrom. To make a measurement the user must position the probe, having both a source of radiation for irradiating the coating and apparatus for detecting the particles backscattered from the coatings, adjacent to the portion of the coating which is to be measured.

A backscatter measurement instrument is connected to the probe for counting the backscattered particles for a preselected time period and giving an indication of the coating thickness corresponding to this count. It is desirable that the probe and the portion of the coated material to be measured remain stationary with respect to one another during this measurement period. The longer this period of measurement the more accurate the result.

In the electronic industry manufacturers of coated substrates have developed efficient and economical processes for coating strips of substrate material. This is a highly developed art where coatings can be applied in the range of 30–100 micro inches with a high degree of uniformity. It has been determined that coating strips of substrate material is much more economical than coating substrates on a piece basis.

In recent years, there has been a particular need for an instrument for accurately measuring thickness of coatings on substrate materials, because gold is used for contact points in electronic circuits, and the price of gold has risen considerably. Accordingly, there has been an increased demand for accurate instruments to determine how much gold is being deposited in the coating process.

The process of coating strips of substrate material is a continuous one where the substrate material moves at a predetermined speed through the coating stage. Since the probe is preferably stationary with respect to the coated strip of substrate material during the backscatter thickness measurement period, it is necessary, with conventional instruments, to stop the coating process while the measurement is being made and then start it up again. This discontinuous stop and start process is quite time consuming and there has been a need for a device which could measure the coating thickness without having to stop the movement of the strip of substrate material.

SUMMARY OF THE INVENTION

The present invention overcomes the disadvantages of these conventional instruments by providing a measurement wheel for positioning a probe in stationary relation to a portion of the coated strip of substrate material to be measured while the coated strip is moving from a feed supply to a takeup location at a predetermined speed.

A probe is mounted on the rim of the measurement wheel and the moving strip of coated substrate material is threaded around the outer surface of the rim. The measurement wheel is rotated at a speed such that the tangential speed of a point on the rim equals the speed of movement of the strip of coated substrate material; thus, the probe and the portion of the coated strip to be measured move in stationary relation to one another until the portion of the coated strip to be measured leaves the rim of the measurement wheel and advances to the take-up location.

While the probe is adjacent the portion of the coated strip to be measured, the probe irradiates the coating and detects the backscattered radiation. A backscatter measuring instrument (not included in the present invention) is connected to the probe. This instrument counts the particles backscattered from the coating during the measurement period selected by the user and converts this backscatter count into indicia of coating thickness. The measurement period may be adjusted by the user, with an upper limit being the time it takes the portion of the coated strip of substrate material to be measured to move from its first engagement with the measurement wheel to the position where it leaves engagement with the measurement wheel.

BRIEF DESCRIPTION OF THE DRAWINGS

In order that the invention may be clearly understood and readily carried into effect, a preferred embodiment will now be described, by way of example only, with reference to the accompanying drawings wherein.

DESCRIPTION OF A PREFERRED EMBODIMENT

Figure 1:
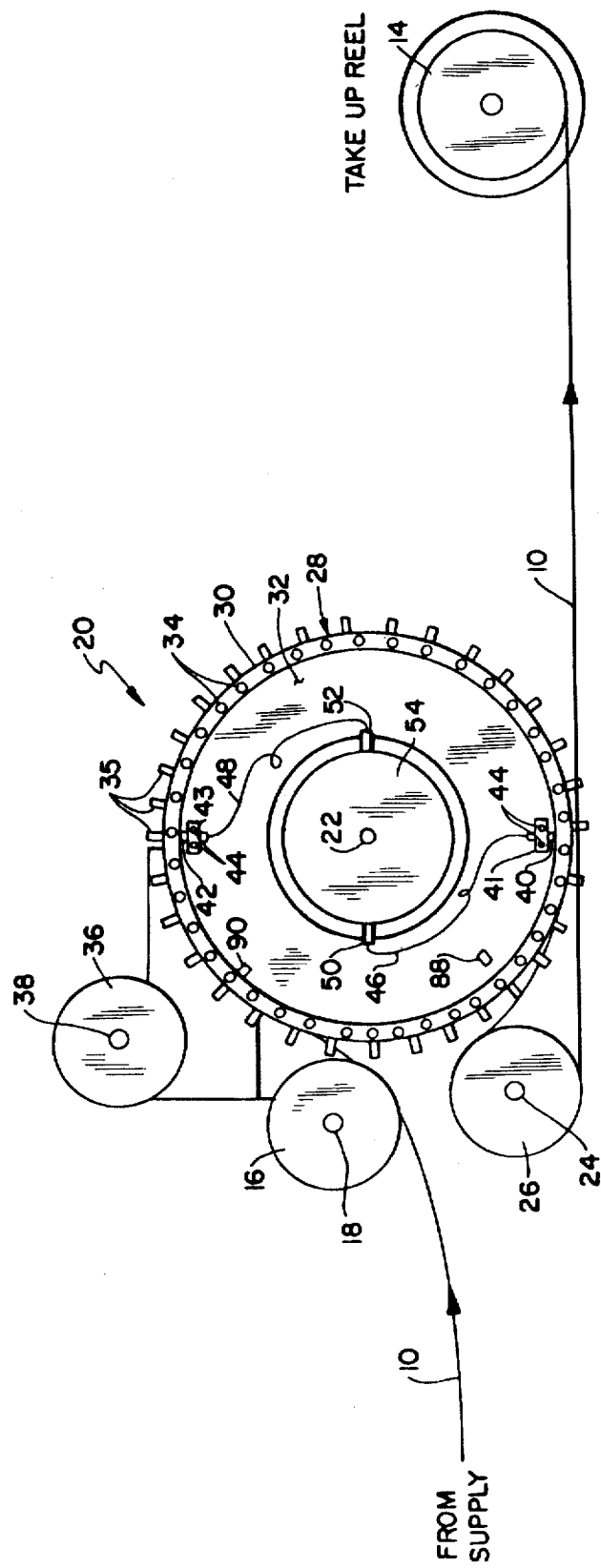
FIG. 1 is a schematic front view of the apparatus according to the present invention.

In the embodiment illustrated in FIG. 1, the path of a continuous strip of coated substrate material 10 is shown moving from a supply (not shown) to a take-up reel 14 in the direction of the arrows. The supply may be, for example, plating tanks for coating substrate material.

The strip 10 is threaded from the supply past a freely rotating guide wheel 16 mounted on axle 18, around a freely rotating measurement wheel 20 mounted on axle 22, around another freely rotating guide wheel 24 mounted on axle 26 and then to the take-up reel 14.

Figure 2:
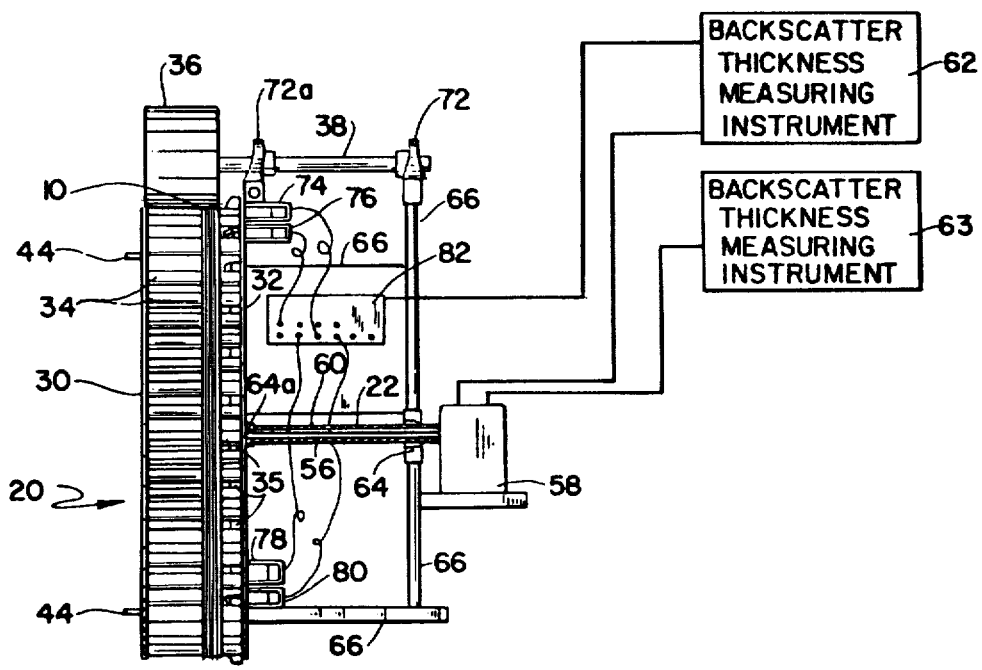
FIG. 2 is a schematic right hand side view of the apparatus illustrated in FIG. 1 omitting the take-up reel.
Figure 3:
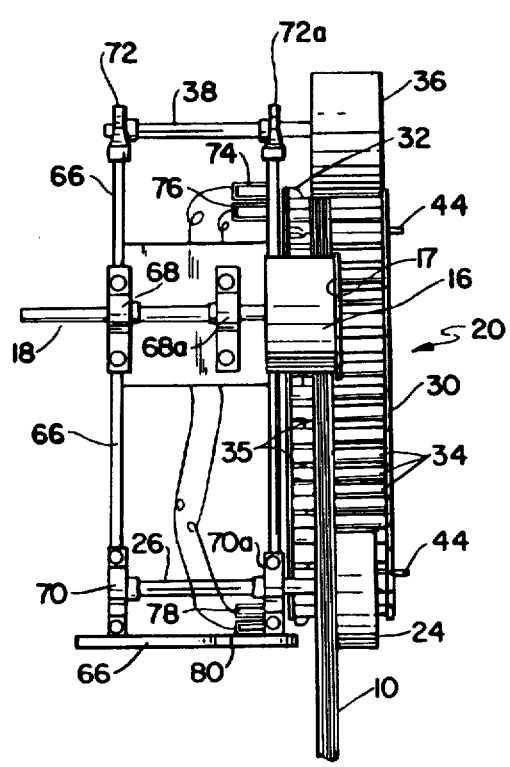
FIG. 3 is a schematic left hand view of the apparatus illustrated in FIG. 1.

In the preferred embodiment, take-up reel 14 is rotatably driven in the direction of the arrow by a motor (not shown). The strip of substrate material travelling through the plating tanks is subject to drag forces which maintain the strip 10 in tension when strip 10 is drawn to the take-up reel 14. The measurement wheel 20 has a rim 28 having an annular side support 30 and disk 32 separated by rubber covered rods 34. Mounted on the disk 32 are strip guide bars 35 for guiding an edge of the strip 10 on the measurement wheel 20 as shown in FIG. 2. In addition, a guide rim 17 on guide wheel 16 guides the other edge of strip 10 on the measurement wheel as shown in FIG. 3.

Since the strip 10 is in tension, the strip 10 when moving at a predetermined speed from the supply to the take-up reel 14 frictionally engages the rubber covered rods 34 and rotates the freely rotatable measurement wheel 20 about its axle 22. Thus the speed of rotation of the measurement wheel 20 is such that a point on the strip 10 and an adjacent point on the rim 28 of the measurement wheel 20 are stationary relative to one another while the strip 10 moves around the axle 22 or measurement wheel 20.

The guide wheel 36 mounted on axle 38 is not used when the strip 10 is threaded as shown in FIG. 1. However, guide wheel 36 would be used and guide wheel 24 would not be used if strip 10 were threaded around measurement wheel 20 in the opposite direction, so as to measure coating thickness on the other face of the strip 10.

Probe 40 and probe 42 shown schematically in FIG. 1 are mounted in probe holders 41 and 43 respectively on rim 28 of measurement wheel 20. The probes 40 and 42 extend between the rubber covered rods 34 to a position in close proximity to or in contact with the strip 10. These probes are of conventional construction such as Probe Model HH-3 manufactured by Unit Process Assemblies, Inc. and include sources of radiation for irradiating the coated substrate and means for detecting the radiation backscattered from the coated substrate. The probe holders 41 and 43 are preferably mounted on rods 44 attached to the rim 28 as shown in FIGS. 1 and 2. This permits the probes 40 and 42 to be moved across the face of the strip 10 so that the probes can be positioned for measurement at any lateral position on the strip 10.

The probes 40 and 42 are connected by wires 46 and 48 to sockets 50 and 52 on hub 54. A cable 56 connected to sockets 50 and 52 carries electrical signals corresponding to the backscattered particles detected by probes 40 and 42 to slip ring connector 58 through a channel 60 grooved in axle 22. The other side of the slip ring connector 58 is connected to a backscatter thickness measuring instrument 62 associated with probe 40 and a backscatter thickness measuring instrument 63 associated with probe 42. These backscatter measuring instruments may be, for example, the instruments described in U.S. patent application Ser. No. 631,412 filed Nov. 12, 1975.

The axle 22 of measurement wheel 20 is supported by journal bearings 64 and 64a which in turn are supported by frame 66 as shown in FIG. 2. The axle 18 of guide wheel 16 is supported by journal bearings 68 and 68a; the axle 26 of guide wheel 24 by journal bearings 70 and 70a; and the axle 38 of guide wheel 36 by journal bearings 72 and 72a. These journal bearings are supported in turn by frame 66 as shown in FIG. 3. In addition, the journal bearings 68 and 68a are constructed such as to permit axial movement of axle 18 supporting guide wheel 16 to accommodate different widths of strip 10. Strip 10 is guided around measurement wheel 20 between guide rim 17 of guide wheel 16 and guide bars 35. When guide wheel 16 is moved to the right in FIG. 3 a wider strip 10 may be accommodated. Once the axle 18 is appropriately positioned, set screws (not shown) lock the axle 18 in this position.

The backscatter radiation counting apparatus included in the backscatter thickness measuring instruments 62 and 63 are actuated by the magnetic switches 74, 76, 78 and 80 as described below. These magnetic switches are connected to the backscatter thickness measuring instruments 62 and 63 through the junction board 82 as shown in FIG. 2.

Mounted on the disk 32 of measuring wheel 20 are two magnets 88 and 90. Magnet 90 is mounted near the rim 28 in a position such that it is aligned to activate magnetic switches 74 and 80 when the measurement wheel 20 is rotating. Magnet 88 is mounted in alignment with magnetic switches 76 and 78 to activate these switches when measurement wheel 20 is rotating. There is a switching means (not shown) on the junction board 82 for selectively activating the pair of magnetic switches 76 and 78 or the pair of magnetic switches 74 and 80 depending on whether the measurement wheel is to be rotated clockwise or counterclockwise.

In the set-up as shown in FIG. 1 where the measurement wheel 20 is rotated clockwise, the magnetic switches 76 and 78 are activated and the magnetic switches 74 and 80 are deactivated.

The sequence of events is then as follows:

(1) When magnet 88 passes magnetic switch 78, the measurement period for probe 42 commences and counting of backscattered radiation detected by probe 42 is initiated.

(2) When magnet 88 passes magnetic switch 76, the measurement period for probe 40 is commenced and counting of backscattered radiation detected by probe 40 is initiated.

When the measurement wheel 20 is set up to rotate in the counter-clockwise direction, the magnetic switches 74 and 80 are activated and magnetic switches 76 and 78 are deactiveted by the switching means (not shown) on junction board 82. In this set up magnet 90 activates magnetic switches 74 and 80 to commence the measurement periods for probes 40 and 42 respectively.

The measurement continues for the duration of the measurement period selected by the user on the corresponding backscatter measurement instruments 62 and 63.

With the above described device, a user may make thickness measurements of a strip of coated substrate material moving continuously. Thus, measurements can be made on-line to monitor the coating process.

While the fundamental novel features of the invention have been shown and described, it should be understood that various substitutions, modifications and variations may be made by those skilled in the art without departing from the spirit or scope of the invention. Accordingly, all such modifications and variations are included in the scope of the invention as defined by the following claims.

I claim:

1. A backscatter thickness measuring apparatus for measuring the thickness of a coating on a strip of substrate material moving at a predetermined speed from a feed supply to a take-up location comprising:

a probe means for irradiating a portion of the coating on the strip of substrate material and detecting the backscatter radiation from such portion during a measurement period;

a probe holder moveable with the moving strip of substrate material for holding the probe means in adjacent stationary relation with such portion of the coating on the strip of substrate material during the measurement period; and counting and measurement means connected to the probe means for counting the backscatter radiation during the measurement period and determining the thickness of the coating of such portion in accordance with the backscatter count.

2. The backscatter thickness measuring apparatus according to claim 1 further including means for positioning the probe means laterally across the strip of substrate material.

3. A backscatter thickness measuring apparatus for measuring the thickness of a coating on a strip of substrate material moving at a predetermined speed from a feed supply to a take-up location comprising:
   probe means for irradiating a portion of the coating on the strip of substrate material and detecting the backscatter radiation from such portion during a measurement period;
   counting and measurement means connected to the probe means for counting the backscatter radiation during the measurement period and determining the thickness of the coating of such portion in accordance with the backscatter count;
   means for positioning the probe means at a first position whereby the probe means is held adjacent the strip prior to the measurement period;
   means for stripping the probe means away from the moving strip of substrate material after the measurement period and returning the probe means to the first position prior to the commencement of a new measurement period.

4. A method utilizing backscatter apparatus for measuring the thickness of a coating on a strip of substrate material moving at a predetermined speed from a feed supply to a take-up location comprising:
   irradiating a portion of the coating on the strip of substrate material with a backscatter probe and detecting the backscatter radiation from such portion during a measurement period;
   moving the backscatter probe in adjacent stationary relation with such portion of the coating on the strip of substrate material during the measurement period;
   counting the backscatter radiation during the measurement period; and
   determining the thickness of the coating of such portion in accordance with the backscatter count.

5. The method according to claim 4 including the further step of positioning the backscatter probe laterally across the strip of substrate material.

6. A method of utilizing backscatter apparatus for measuring the thickness of a coating on a strip of substrate material moving at a predetermined speed from a feed supply to a take-up location comprising:
   irradiating a portion of the coating on the strip of substrate material with a backscatter probe and detecting the backscatter radiation from such portion during a measurement period;
   positioning the backscatter probe at a first position whereby the backscatter probe is held adjacent the strip prior to the measurement period;
   moving the backscatter probe in adjacent stationary relation with the strip of substrate material during the measurement period;
   counting the backscatter radiation during the measurement period;
   determining the thickness of the coating of such portion in accordance with the backscatter count;
   stripping the backscatter probe from the moving strip of substrate material after the measurement period;
   returning the backscatter probe to the first position prior to the commencement of a new measurement period.

7. The method according to claim 6 further including the step of positioning the backscatter probe laterally across the strip of substrate material.

* * * * *